(12) United States Patent
Okaguchi et al.

(10) Patent No.: US 8,156,814 B2
(45) Date of Patent: Apr. 17, 2012

(54) SURFACE ACOUSTIC WAVE SENSOR

(75) Inventors: Kenjiro Okaguchi, Moriyama (JP); Michio Kadota, Kyoto (JP); Koji Fujimoto, Otsu (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 224 days.

(21) Appl. No.: 12/505,571

(22) Filed: Jul. 20, 2009

(65) Prior Publication Data
US 2009/0272193 A1 Nov. 5, 2009

Related U.S. Application Data

(63) Continuation of application No. PCT/JP2008/050363, filed on Jan. 15, 2008.

(30) Foreign Application Priority Data

Feb. 19, 2007 (JP) .................................. 2007-038064

(51) Int. Cl.
*G01N 29/036* (2006.01)
*H01L 41/04* (2006.01)

(52) U.S. Cl. .......................................... 73/657; 73/579

(58) Field of Classification Search ............. 73/579, 73/54.23–54.27, 61.49, 24.01, 24.06, 61.75, 73/64.53, 657; 310/311, 313 R, 313 B, 313 C
See application file for complete search history.

(56) References Cited

U.S. PATENT DOCUMENTS

| | | | |
|---|---|---|---|
| 6,836,196 B2* | 12/2004 | Kadota et al. | 333/193 |
| 7,168,298 B1* | 1/2007 | Manginell et al. | 73/54.25 |
| 7,389,673 B2* | 6/2008 | Kimura et al. | 73/24.06 |
| 7,437,907 B2* | 10/2008 | Kimura et al. | 73/24.06 |
| 7,656,070 B2* | 2/2010 | Kadota et al. | 310/313 R |
| 7,762,124 B2* | 7/2010 | Okaguchi et al. | 73/61.49 |
| 2003/0141947 A1 | 7/2003 | Kadota et al. | |
| 2004/0133348 A1 | 7/2004 | Kalantar-Zadeh et al. | |
| 2004/0226162 A1 | 11/2004 | Miura et al. | |
| 2006/0071579 A1 | 4/2006 | Kando | |
| 2007/0085629 A1 | 4/2007 | Kando | |
| 2007/0107516 A1 | 5/2007 | Fujimoto et al. | |

FOREIGN PATENT DOCUMENTS

| | | |
|---|---|---|
| JP | 5-5689 A | 1/1993 |
| JP | 6-194346 A | 7/1994 |

(Continued)

OTHER PUBLICATIONS

Official Communication issued in International Patent Application No. PCT/JP2008/050363, mailed on May 1, 2008.

Freudenberg et al., "A SAW immunosensor for operation in liquid using a SiO2 protective layer," Sensors and Actuators B, vol. 76, 2001, pp. 147-151, Heidelberg, Germany.

(Continued)

*Primary Examiner* — J M Saint Surin
(74) *Attorney, Agent, or Firm* — Keating & Bennett, LLP

(57) ABSTRACT

A surface acoustic wave sensor detects a mass load on a resonator-type surface acoustic wave filter on the basis of a change in frequency and includes an IDT electrode arranged on a piezoelectric substrate to excite surface waves, an insulating film arranged so as to cover the IDT electrode, and a reaction film which is disposed on the insulating film and which reacts with a target substance to be detected or a binding substance that binds to a target substance to be detected. The reaction film is composed of a metal or a metal oxide.

8 Claims, 6 Drawing Sheets

FOREIGN PATENT DOCUMENTS

| | | | |
|---|---|---|---|
| JP | 2003-258602 | A | 9/2003 |
| JP | 2004-526977 | A | 9/2004 |
| JP | 2004-340766 | A | 12/2004 |
| JP | 2005-189213 | A | 7/2005 |
| JP | 2006-220508 | A | 8/2006 |
| WO | 2005/003752 | A1 | 1/2005 |
| WO | 2005/099091 | A1 | 10/2005 |

OTHER PUBLICATIONS

Official Communication issued in corresponding Japanese Patent Application No. 2009-500103, mailed on Jun. 29, 2010.
Official Communication issued in corresponding Chinese Patent Application No. 200780048146.1, mailed on Sep. 29, 2011.

* cited by examiner

SURFACE ACOUSTIC WAVE SENSOR

BACKGROUND OF THE INVENTION

1. Field of the Invention

The present invention relates to a surface acoustic wave sensor arranged to detect a target substance on the basis of a change in frequency due to mass load. More particularly, the present invention relates to a surface acoustic wave sensor including a reaction film arranged to react with a target substance to be detected or a binding substance that binds to a target substance to be detected.

2. Description of the Related Art

To date, various sensors using surface acoustic wave devices have been proposed. For example, WO2005/003752 discloses a surface acoustic wave sensor having a structure, a cross-sectional front view of which is schematically shown in FIG. 12.

In a surface acoustic wave sensor 501, an IDT electrode 503 is disposed on a piezoelectric substrate 502 in order to excite surface acoustic waves. The IDT electrode 503 includes a main electrode layer 503a composed of Au or the like, and adhesion layers 503b and 503c composed of Ti or the like disposed on the upper surface and the lower surface of the main electrode layer 503a. A protective film 504 composed of $SiO_2$ is disposed so as to cover the IDT electrode 503.

A reaction film 505 mainly composed of an organic material, such as a synthetic resin, is disposed on the protective film 504. The reaction film 505 is composed of a resin composition prepared by mixing a reactant which reacts with a target substance to be detected into a synthetic resin.

When a liquid containing a target substance to be detected or the like is brought into contact with the reaction film 505, the target substance to be detected binds to the reaction film 505. As a result, the mass load on the IDT electrode 503 increases. Due to the change in the mass load, the frequency of a surface acoustic wave excited by the IDT electrode 503 changes. The target substance to be detected can be detected on the basis of the change in frequency.

The adhesion layer 503b is provided in order to enhance the adhesion of the IDT electrode 503 to the piezoelectric substrate 502, and the adhesion layer 503c is provided in order to enhance the adhesion of the IDT electrode 503 to the protective film 504. The protective film 504 is provided in order to protect the IDT electrode 503.

In the surface acoustic wave sensor 501 described in WO2005/003752, a target substance to be detected is bound to the reaction film 505. However, the reaction film 505 is composed of an organic material, and therefore, when a liquid containing the target substance to be detected comes into contact with the surface of the reaction film 505, the liquid component, e.g., water, tends to permeate through the reaction film 505, be absorbed by the protective film 504, and reach the IDT electrode 503. Furthermore, the adhesion layer 503c composed of Ti or the like may absorb moisture, and as a result, the frequency of the surface acoustic wave excited tends to vary. That is, the drift of the frequency characteristic increases, and it becomes difficult to detect with high accuracy a change in frequency due to a small change in the mass load.

SUMMARY OF THE INVENTION

Preferred embodiments of the present invention provide a resonator-type surface acoustic wave sensor which can eliminate the drawbacks in the conventional art described above and which can detect a target substance to be detected with high accuracy even when the change in the mass load due to the target substance to be detected is small.

According to a preferred embodiment of the present invention, a surface acoustic wave sensor detects a mass load on a resonator-type surface acoustic wave filter on the basis of a change in frequency and includes a piezoelectric substrate, a surface wave exciting electrode disposed on the piezoelectric substrate, an insulating film arranged on the piezoelectric substrate so as to cover the surface wave exciting electrode, and a reaction film arranged on the insulating film so as to react with a target substance to be detected or a binding substance that binds to a target substance to be detected. The reaction film is composed of a metal or a metal oxide. The reaction by the reaction film is not limited to reactions due to chemical or biochemical binding, but widely includes reactions due to adsorption, occlusion, fixation, etc.

In the surface acoustic wave sensor according to a preferred embodiment of the present invention, preferably, the piezoelectric substrate is composed of $LiTaO_3$, the insulating film is composed of $SiO_2$ or SiN, and the thickness of the insulating film normalized by the wavelength of a surface acoustic wave of the surface wave exciting electrode is in a range of about 0.1 to about 0.45, for example. In such a case, it is possible to decrease the absolute value of the temperature coefficient of frequency TCF. Therefore, it is possible to decrease the variation of the characteristics of the surface acoustic wave sensor due to a change in temperature.

In the surface acoustic wave sensor according to a preferred embodiment of the present invention, preferably, the piezoelectric substrate is composed of $LiNbO_3$, the insulating film is composed of $SiO_2$ or SiN, and the thickness normalized by the wavelength of a surface acoustic wave of the surface wave exciting electrode is in a range of about 0.25 to about 1.125, for example. In such a case, it is possible to decrease the absolute value of the temperature coefficient of frequency TCF. Therefore, it is possible to decrease the variation of the characteristics of the surface acoustic wave sensor due to a change in temperature.

In the surface acoustic wave sensor according to a preferred embodiment of the present invention, preferably, the reaction film is composed of one metal selected from the group consisting of Ni, Cu, Co, and Zn. In such a case, moisture can be prevented from entering the surface acoustic wave sensor. Consequently, the variation of the frequency characteristic due to the moisture absorption of the protective film and the adhesion layer composed of Ti or the like can be further decreased. Furthermore, by appropriately selecting the reaction film, binding to a certain target substance to be detected, such as a histidine-tagged protein, can be performed.

In the surface acoustic wave sensor according to a preferred embodiment of the present invention, preferably, the reaction film is composed of one metal selected from the group consisting of Pd, PdNi, and TiFe. In such a case, moisture can be prevented from entering the surface acoustic wave sensor, and the variation of the frequency characteristic due to the moisture absorption of the insulating film, etc. can be decreased. It is also possible to detect a gas, such as hydrogen gas by using these metals.

In the surface acoustic wave sensor according to a preferred embodiment of the present invention, preferably, the reaction film is composed of one metal or metal oxide selected from the group consisting of ZnO, SnO, and Pt. In such a case, it is also possible to provide a surface acoustic wave sensor in which the variation of the frequency characteristic does not easily occur, and which is also suitable for detecting a gas, such as carbon monoxide gas.

In the surface acoustic wave sensor according to a preferred embodiment of the present invention, preferably, the reaction film is composed of $ZrO_2$. In such a case, the variation of the frequency characteristic does not easily occur, and also it is possible to detect with high accuracy a nitrogen oxide as a target substance to be detected.

The surface wave exciting electrode used in the surface acoustic wave sensor according to a preferred embodiment of the present invention can be composed of various metals, and preferably contains, as a main component, a metal that is heavier than Al, such as Au, Pt, Cu, Ta, or W. Thereby, even when the normalized thickness of the $SiO_2$ film is in the range of, for example, about 0.1 to about 0.45 (in the case of $LiTaO_3$) or in the range of, for example, about 0.25 to about 1.125 (in the case of $LiNbO_3$), the formation can be made without degrading the frequency characteristic.

A surface acoustic wave sensor according to various preferred embodiments of the present invention detects a mass load on a resonator-type surface acoustic wave filter on the basis of the change in frequency, the resonator-type surface acoustic wave filter including a piezoelectric substrate and a surface wave exciting electrode disposed on the piezoelectric substrate. Consequently, it is possible to reduce the size of the sensor in comparison with a surface acoustic sensor including a transversal type surface acoustic wave filter.

Moreover, according to a preferred embodiment of the present invention, the surface wave exciting electrode is protected by the insulating film described above, and a reaction film, which reacts with a target substance to be detected or a binding substance that binds to a target substance to be detected, is disposed on the insulating film, the reaction film being composed of a metal or a metal oxide. Consequently, in comparison with the case where no metal film is used and an insulting film is thin, the resistance to moisture absorption of the insulating film itself or an adhesion film composed of Ti or the like is greatly improved. Therefore, the variation, i.e., drift, of the frequency characteristic due to moisture absorption does not easily occur. Thus, even if the change in the mass load is small, it is possible to detect with high accuracy a substance to be detected.

Other features, elements, steps, characteristics and advantages of the present invention will become more apparent from the following detailed description of preferred embodiments of the present invention with reference to the attached drawings.

DETAILED DESCRIPTION OF THE PREFERRED EMBODIMENTS

Hereinafter, the present invention is disclosed by specifically describing preferred embodiments of the present invention with reference to the drawings.

Figure 1:
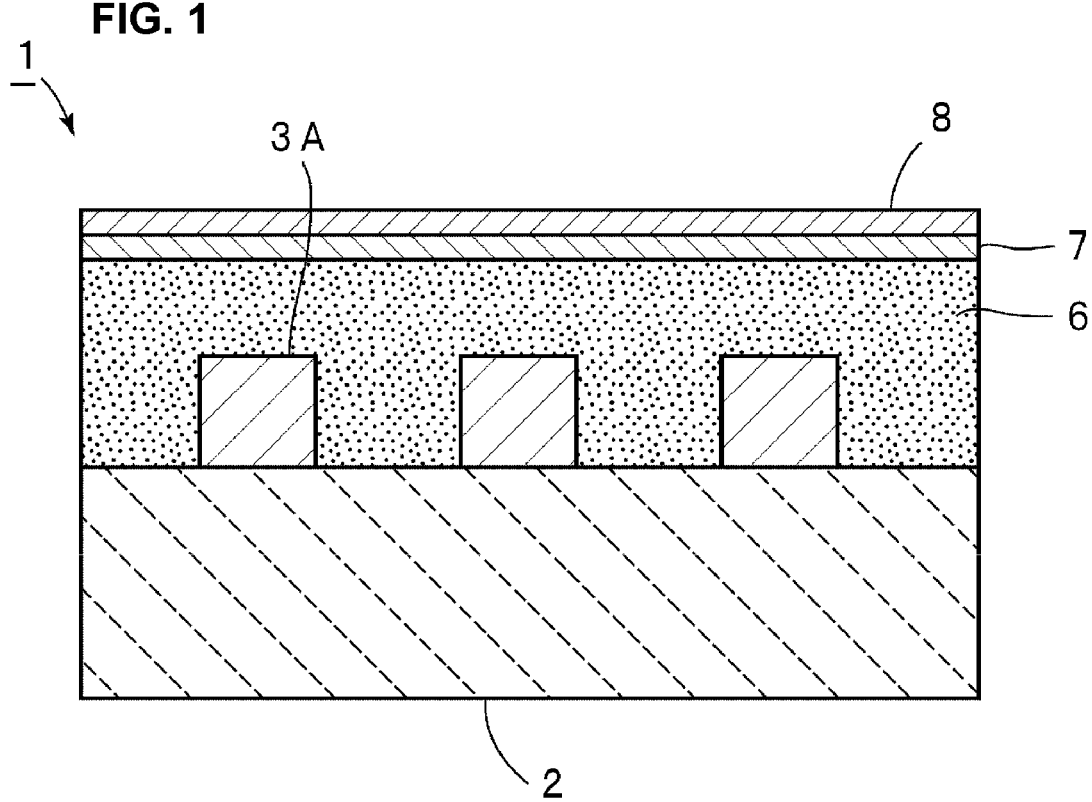
FIG. 1 is a schematic cross-sectional front view showing a main portion of a surface acoustic wave sensor according to a first preferred embodiment of the present invention.
Figure 2:
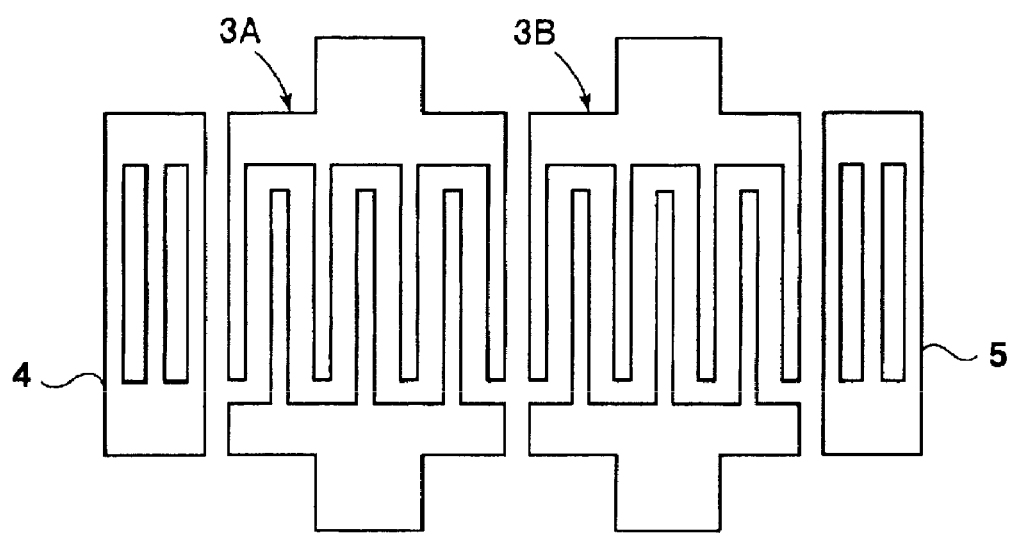
FIG. 2 is a schematic plan view showing an electrode structure of the surface acoustic wave sensor according to the first preferred embodiment of the present invention.

FIG. 1 is a schematic cross-sectional front view showing a surface acoustic wave sensor according to a first preferred embodiment of the present invention, and FIG. 2 is a schematic plan view showing an electrode structure thereof.

A surface acoustic wave sensor 1 includes a piezoelectric substrate 2. In this preferred embodiment, the piezoelectric substrate 2 is preferably composed of $LiTaO_3$. The piezoelectric substrate 2 may be composed of another piezoelectric single crystal, such as $LiNbO_3$ or quartz crystal. Furthermore, the piezoelectric substrate 2 may be composed of a piezoelectric ceramic, such as a PZT-based ceramic.

Preferably, when a material having a positive temperature coefficient, such as $SiO_2$, is used for an insulating film, the piezoelectric substrate 2 is preferably composed of a piezoelectric material having a negative temperature coefficient of frequency, such as $LiTaO_3$ or $LiNbO_3$.

An electrode structure for surface wave excitation shown in FIG. 2 is disposed on the piezoelectric substrate 2. The electrode structure includes IDT electrodes 3A and 3B serving as surface wave exciting electrodes, and reflectors 4 and 5 located on both sides in the surface acoustic wave propagating direction of the region where the IDT electrodes 3A and 3B are provided. In the surface acoustic wave sensor 1 according to this preferred embodiment, the IDT electrodes 3A and 3B and the reflectors 4 and 5 constitute a resonator-type surface acoustic wave filter device. FIG. 1 shows a schematic cross-sectional front view of a portion in which the IDT electrode 3A is provided.

Figure 10:
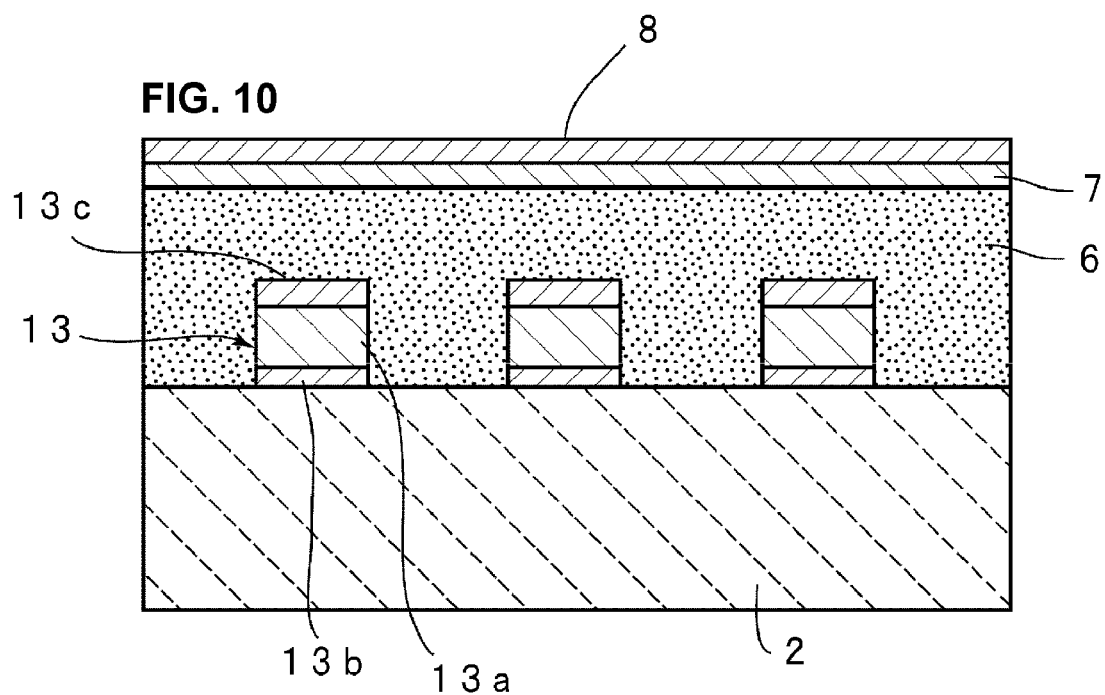
FIG. 10 is a schematic cross-sectional front view showing a modification example in which an IDT electrode is composed of a laminated metal film.

In this preferred embodiment, the IDT electrodes 3A and 3B and the reflectors 4 and 5 are composed of Au. The IDT electrodes 3A and 3B and the reflectors 4 and 5 may be composed of a metal other than Au, for example, Pt, Ag, or Cu, or may be composed of an alloy mainly containing these metals. Furthermore, as schematically shown in FIG. 10, an electrode 13, such as an IDT electrode or a reflector, may be composed of a laminated metal film in which a plurality of metal films 13a to 13c are laminated.

Preferably, the IDT electrodes 3A and 3B and the reflectors 4 and 5 contain, as a main component, a metal heavier than Al, for example, Au, Pt, Cu, Ta, or W. Examples of the IDT electrodes 3A and 3B and the reflectors 4 and 5 containing Au as a main component include those composed of Au or an alloy containing Au as a main component, and in the case of a laminated metal film, those having a structure in which Au or an alloy film mainly composed of Au occupies the main portion of the laminated metal film.

An insulating film 6 is preferably arranged so as to cover the IDT electrode 3A. The insulating film 6 is also preferably arranged so as to cover the IDT electrode 3B and the reflectors 4 and 5.

The insulating film 6 is provided in order to protect the IDT electrodes 3A and 3B and the reflectors 4 and 5. In this preferred embodiment, the insulating film 6 is composed of $SiO_2$ and has a positive temperature coefficient of frequency TCF. Since the piezoelectric substrate 2 is composed of $LiTaO_3$ and has a negative temperature coefficient of frequency TCF, the combination of the $SiO_2$ film and $LiTaO_3$ makes it possible to decrease the change in the frequency characteristic due to the change in temperature.

An adhesion layer 7 is disposed on the insulating film 6. The adhesion layer 7 is preferably composed of Ti and provided in order to enhance adhesion of a reaction film 8 composed of a metal to be formed on the adhesion layer 7, which will be described below, to the insulating film 6.

The reaction film 8 is disposed on the adhesion layer 7. In this preferred embodiment, the reaction film 8 is preferably composed of Ni. The reaction film 8 composed of Ni adsorbs a histidine-tagged protein, thus enabling reaction.

In the fabrication of a surface acoustic wave sensor 1, IDT electrodes 3A and 3B and reflectors 4 and 5 are formed on a piezoelectric substrate 2 by a known fabrication method of surface acoustic wave devices. Then, a $SiO_2$ film as an insulating film is formed, for example, by PVD or CVD, such as sputtering or vapor deposition, spin-coating, or the like, so as to achieve a thickness of about 560 nm to about 2,540 nm, for example. Next, an adhesion layer 7 composed of Ti or the like is formed on the insulating film 6 by a thin-film forming method, such as sputtering, vapor deposition, or plating so as to achieve a thickness of about 5 nm to about 200 nm, for example. Finally, a reaction film 8 composed of Ni is formed on the adhesion layer 7 also by a thin-film forming method, such as sputtering, vapor deposition, or plating. Although not particularly limited, the thickness of the reaction film 8 is preferably about 5 nm to about 200 nm. If the thickness of the reaction film 8 is too small, there is a possibility that the reaction film cannot react with a target substance to be detected. If the thickness is too large, there is a possibility that the excitation of surface acoustic waves may be inhibited.

In the surface acoustic wave sensor 1 according to this preferred embodiment, the reaction film 8 is composed of Ni, and as described above, the reaction film 8 adsorbs and binds to a histidine-tagged protein. Consequently, in the case where a histidine-tagged protein is contained in a liquid analyte, when the liquid analyte comes into contact with the reaction film 8, the histidine-tagged protein is adsorbed by the reaction film 8.

Next, a method for measuring a histidine-tagged protein using the surface acoustic wave sensor 1 will be described.

First, the frequency characteristic is measured when a reference liquid which does not contain the histidine-tagged protein is brought into contact with the surface acoustic wave sensor 1 in advance.

Then, the liquid analyte containing histidine-tagged protein is brought into contact with the surface acoustic wave sensor 1 so that the histidine-tagged protein is adsorbed onto the reaction film 8, and the frequency characteristic of the surface acoustic wave sensor 1 is measured.

It is possible to detect the presence or absence of the histidine-tagged protein in the analyte on the basis of the difference between the resonance frequency in the frequency characteristic in the case of contact with the reference liquid and the resonance frequency obtained from the frequency characteristic in the case of contact with the liquid analyte containing the histidine-tagged protein.

Furthermore, it is also possible to detect the concentration of the histidine-tagged protein by preparing a calibration curve in advance as described below. That is, using a plurality of known histidine-tagged protein-containing standard analytes having different concentrations, the frequency characteristic of the surface acoustic wave sensor 1 is measured in the same manner as that described above. A calibration curve is prepared on the basis of the difference between the resonance frequency in the case of contact with the reference liquid and each of the different resonance frequencies obtained in the case of contact with the plurality of standard analytes having different concentrations.

Then, the frequency characteristic is measured with respect to an unknown analyte containing the histidine-tagged protein, the difference between the resonance frequency in the frequency characteristic obtained and the resonance frequency obtained from the frequency characteristic of the reference liquid is calculated, and then, on the basis of the calibration curve, the concentration of the histidine-tagged protein is obtained.

Furthermore, in use of the surface acoustic wave sensor 1 according to a preferred embodiment of the present invention, in the case where a liquid analyte does not so much contaminate the surface of the reaction film 8, using one surface acoustic wave sensor 1, detection of presence or absence and/or quantitative determination of a target substance to be detected can be performed. That is, first, using a surface acoustic wave sensor 1, a calibration curve is prepared as described above, and then, using the same surface acoustic wave sensor 1, the frequency characteristic is measured by use of a reference liquid not containing the histidine-tagged protein and prepared in the same manner as in the analyte. Next, using the analyte, the frequency characteristic is measured, the difference in the frequency characteristic between the two is obtained, and then, the quantity of the histidine-tagged protein is determined on the basis of the calibration curve.

However, in analytes, such as histidine-tagged protein-containing analytes, prepared in the biochemical field, there are often cases where other proteins, other viscous components, or the like are mixed in the analyte liquids. Therefore, when an analyte is brought into contact with the reaction film 8, the influence of contamination is unavoidable even if washing is thoroughly conducted. In such a case, a plurality of surface acoustic wave sensors 1 are prepared. First, using a plurality of analytes for preparing a calibration curve, a calibration curve is prepared. Next, using two new surface acoustic wave sensors 1, first, one of the new surface acoustic wave sensors 1 is brought into contact with the reference liquid, and the frequency characteristic is measured. Then, the other new surface acoustic wave sensor 1 is brought into contact with the analyte, i.e., target to be measured, and the frequency characteristic is measured.

In order to measure the frequency characteristic using a surface acoustic wave sensor 1 according to a preferred embodiment of the present invention, an oscillation circuit that drives the surface acoustic wave sensor 1 is connected to the surface acoustic wave sensor 1, and the IDT electrodes 3A and 3B as the exciting electrodes in the surface acoustic wave sensor 1 are excited. Then, the frequency characteristic of the output signal of the surface acoustic wave sensor 1 is measured. In such a case, when the frequency characteristic of the reference liquid and the analyte is measured using two new surface acoustic wave sensors 1 as described above, by determining the difference in the frequency of the output between the two surface acoustic sensors 1 by a frequency counter or the like, the presence or absence and the concentration of the analyte can be detected.

Specific experimental examples will now be described. A 36° Y-cut X-propagation $LiTaO_3$ substrate was used as a piezoelectric substrate 2, and IDT electrodes 3A and 3B and reflectors 4 and 5, each composed of an Au film with a thickness of 170 nm, were formed. The wavelength λ determined by the pitch of the electrode fingers of the IDT electrodes 3A and 3B was 5.64 μm. A $SiO_2$ film was formed by PVD or CVD, such as sputtering or vapor deposition, spin-coating, or the like so as to cover the IDT electrodes 3A and 3B and the reflectors 4 and 5 so that the thickness h satisfied the relationship h/λ=0.3. Furthermore, an adhesion layer 7 composed of Ti with a thickness of 5 nm was formed by PVD or CVD, such as sputtering or vapor deposition, or the like, and a reaction film 8 composed of Ni with a thickness of 10 nm was formed as an uppermost layer by PVD or CVD, such as sputtering or vapor deposition, or the like.

Figure 3:
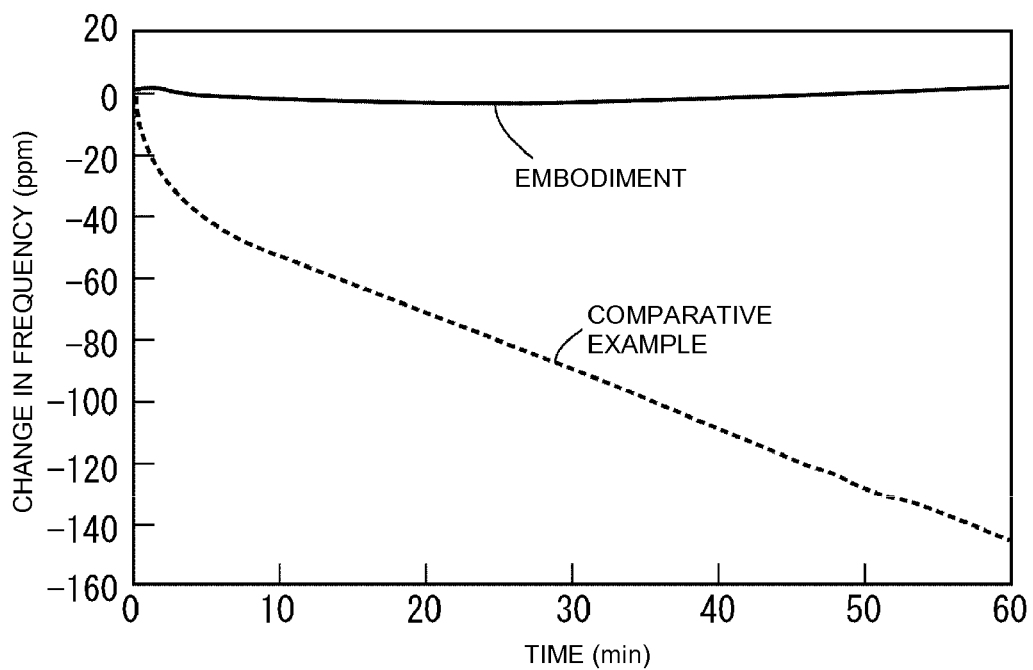
FIG. 3 is a graph showing the change in the frequency characteristic with time of each of a surface acoustic wave sensor according to the first preferred embodiment of the present invention and a surface acoustic wave sensor prepared for comparison.

PBS (Phosphate buffered Saline) as a reference liquid was brought into contact with the surface acoustic wave sensor 1 for 10 minutes, and the variation in the resonance frequency was measured. The results thereof are shown by the solid line in FIG. 3.

Figure 12:
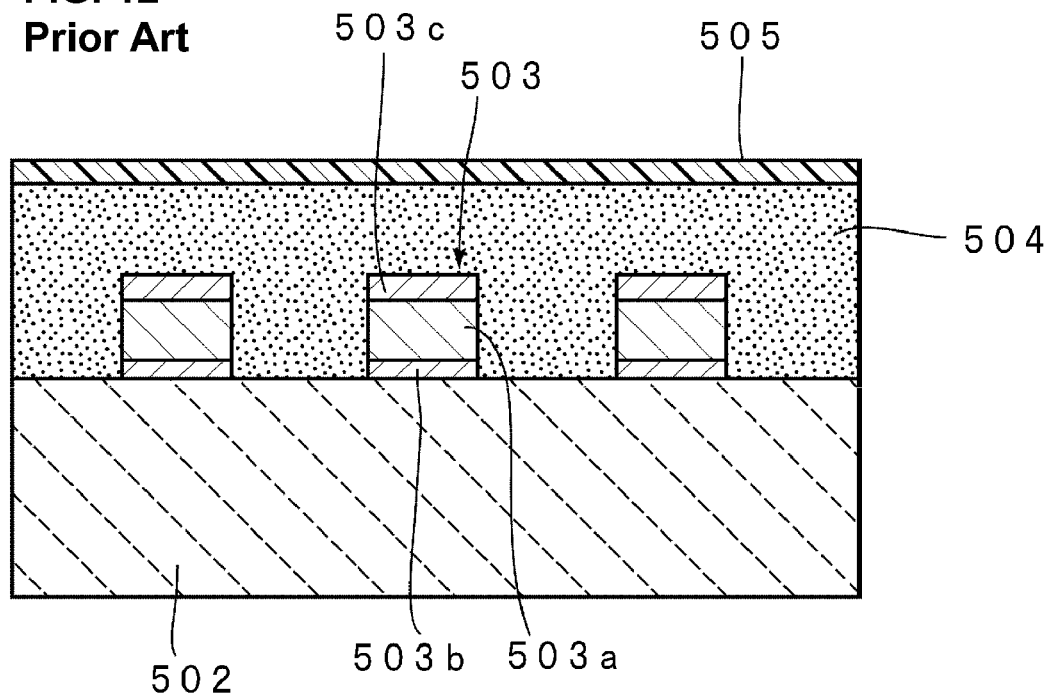
FIG. 12 is a schematic cross-sectional front view showing a conventional surface acoustic wave sensor.

For comparison, a surface acoustic wave sensor having a structure which did not include metal films, such as an adhesion layer composed of Ti and a reaction film composed of Ni, was prepared. That is, a surface acoustic wave sensor 501 shown in FIG. 12 was prepared. The reference liquid was brought into contact with the surface acoustic wave sensor 501 in the same manner as described above, and the resonance frequency was measured. The results thereof are shown by the dashed line in FIG. 3. As is evident from FIG. 3, in the surface acoustic wave sensor prepared for comparison, the resonance frequency gradually decreases in the period until 60 minutes from the start of measurement, thus indicating the occurrence of a large frequency drift. This drift is believed to be caused by moisture absorption. In contrast, in the surface acoustic wave sensor 1 according to this preferred embodiment, there is little change in the resonance frequency even 60 minutes after the start.

Figure 4:
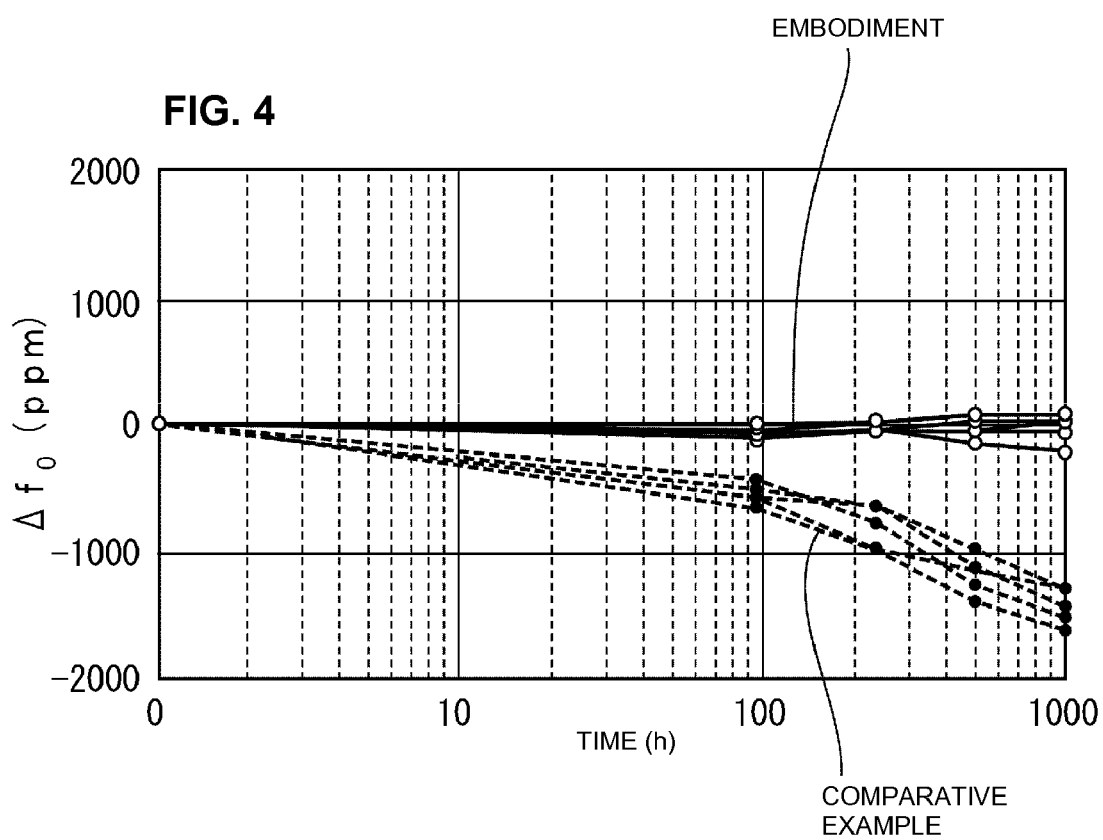
FIG. 4 is a graph showing the change in the frequency characteristic of each of surface acoustic wave sensors according to the first preferred embodiment of the present invention and surface acoustic wave sensors prepared for comparison when left in a humid environment.

Furthermore, a plurality of surface acoustic wave sensors 1 and a plurality of surface acoustic wave sensors for comparison were prepared, and a shelf test under high humidity was carried out in which the sensors were left in an environment at 60° C. and a relative humidity of 95% for 1,000 hours. In the shelf test under high humidity, the resonance frequency was measured after 100 hours, 250 hours, 500 hours, and 1,000 hours, and the amount of change in the resonance frequency $\Delta f_0$ relative to the initial resonance frequency, i.e., $\Delta f_0$=(measured resonance frequency f−initial resonance frequency $f_0$), was calculated for each measurement. The results thereof are shown in FIG. 4. The solid lines in FIG. 4 show the results of the sensors according to the preferred embodiment described above, and the dashed lines show the results of the surface acoustic wave sensors prepared for comparison.

As is evident from FIG. 4, in the surface acoustic wave sensors prepared for comparison, the resonance frequency decreases with time. In contrast, according to the present preferred embodiment, there is little change in the characteristic even after being left for 1,000 hours.

Consequently, it is clear that, in the surface acoustic wave sensors 1 according to this preferred embodiment, even after being stored for a long period of time, the change in the frequency characteristic can be significantly reduced.

Figure 5:
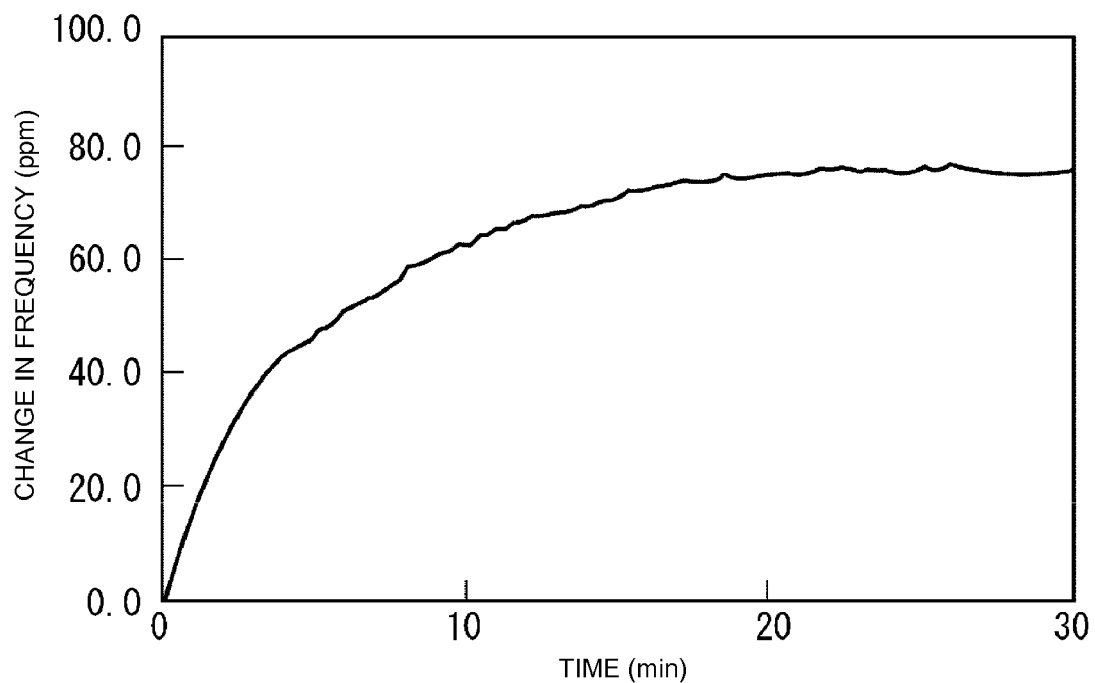
FIG. 5 is a graph showing the change in the resonance frequency when a PBS buffer solution containing a histidine-tagged protein as an analyte is brought into contact with a reaction film of a surface acoustic wave sensor according to the first preferred embodiment of the present invention.

Next, in the surface acoustic wave sensor 1 according to the preferred embodiment described above, using a histidine-tagged protein solution having a histidine-tagged protein concentration of 0.04 mg/ml and containing 8 mol/l of urea as a denaturant was used as an analyte, the analyte was brought into contact with the surface acoustic wave sensor, and the resonance frequency was measured. FIG. 5 is a graph showing the change in the resonance frequency in a period of 30 minutes. In FIG. 5, the vertical axis indicates the amount of change in the frequency relative to the initial resonance frequency $f_0$.

As is evident from FIG. 5, when the analyte is brought into contact with the sensor, as the binding due to adsorption of the histidine-tagged protein, which is the target-binding substance in the analyte, proceeds, the resonance frequency changes, and after about 20 minutes, the change in the frequency is saturated substantially and stabilized.

Furthermore, in order to allow the histidine-tagged protein to stably adsorb to the reaction film 8 composed of Ni, preferably, ionized $Ni^{+2}$ is fixed onto the reaction film 8 via a chelating agent, such as nitrilotriacetic acid (NTA). Thereby, the histidine-tagged protein is more reliably adsorbed to the reaction film, and the measurement can be conducted with higher accuracy.

Second Preferred Embodiment

A surface acoustic wave sensor according to a second preferred embodiment was obtained as in the first preferred embodiment except that, as the reaction film 8, instead of Ni, a Pd film capable of occluding hydrogen was formed by PVD or CVD, such as sputtering or vapor deposition, for example. In the surface acoustic wave sensor according to the second preferred embodiment, since the reaction film 8 is composed of Pd, a hydrogen occlusion effect is exhibited. Thus, the surface acoustic wave sensor can be used as a sensor for detecting hydrogen gas. This will be described on the basis of a specific experimental example.

Figure 6:
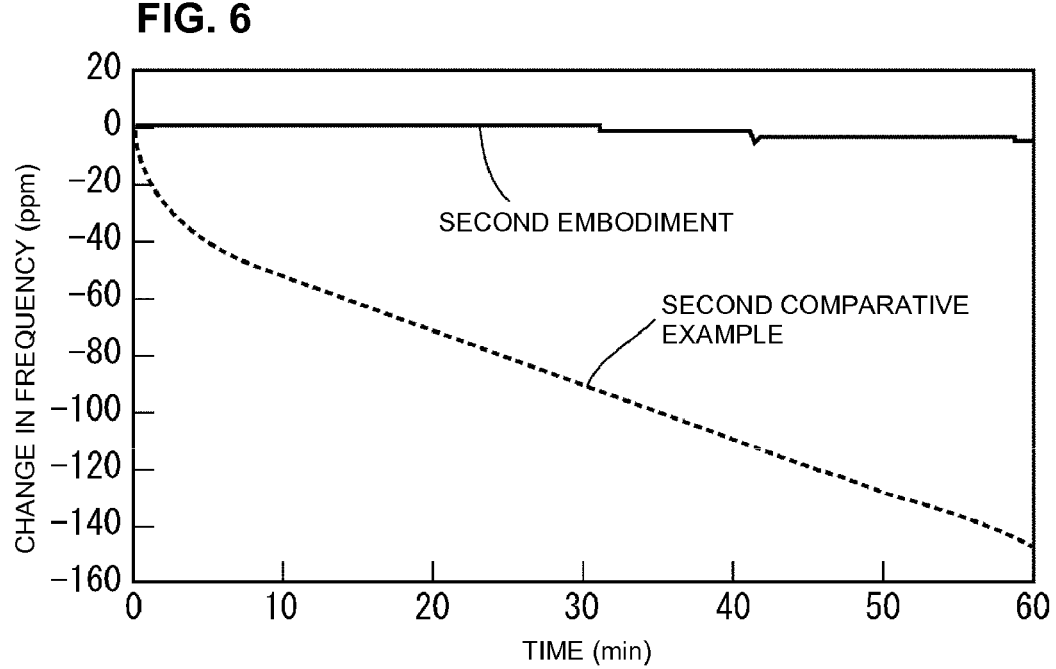
FIG. 6 is a graph showing the change in the frequency characteristic with time of each of a surface acoustic wave sensor according to a second preferred embodiment of the present invention and a surface acoustic wave sensor of a second comparison example prepared for comparison.

A reaction film was formed as in the experimental example of the first preferred embodiment except that, instead of the reaction film composed of a Ni film with a thickness of 10 nm, a reaction film composed of Pd with a thickness of 50 nm was formed by PVD or CVD, such as sputtering or vapor deposition. In an environment at 60° C. and a relative humidity of 95%, as the initial frequency characteristic of the surface acoustic wave sensor according to the second preferred embodiment, the resonance frequency was measured for 60 minutes. For comparison, a surface acoustic wave sensor of a second comparative example having a structure which did not include metal films, such as an adhesion layer composed of Ti and a reaction film composed of Pd, was prepared, and the resonance frequency was measured for 60 minutes under the same conditions. The results thereof are shown in FIG. 6. The solid line in FIG. 6 shows the results of the second preferred embodiment, and the dashed line shows the results of the second comparative example.

Furthermore, as in the shelf test under high humidity in the first preferred embodiment, a plurality of surface acoustic wave sensors according to the second preferred embodiment and a plurality of surface acoustic wave sensors of the second comparative example were prepared, and a shelf test under high humidity was carried out, in which the amount of change in the frequency $\Delta f_0$ was measured. The results thereof are shown in FIG. 7.

Figure 7:
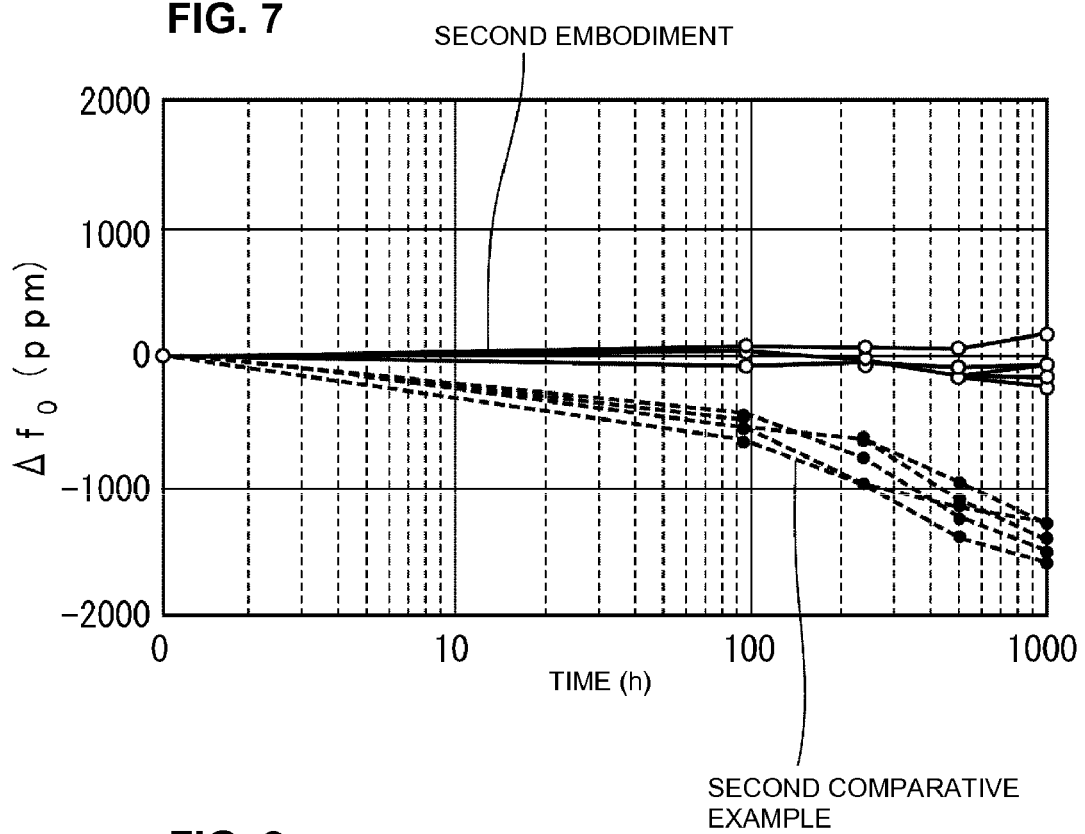
FIG. 7 is a graph showing the change in the frequency characteristic of each of surface acoustic wave sensors according to the second preferred embodiment of the present invention and surface acoustic wave sensors of the second comparative example prepared for comparison when left in a humid environment.

As is evident from FIGS. 6 and 7, in the second preferred embodiment, in comparison with the surface acoustic wave sensors of the second comparative example, the change in the characteristic with time is small, and variations in the characteristic during a long time storage can be prevented. The reason for this is that, in the second preferred embodiment, since the reaction film is also composed of Pd, i.e., a metal, moisture can be prevented from entering the IDT electrodes 3A and 3B and the insulating film 6. That is, since the hygroscopicity is low, the variation in the frequency characteristic does not easily occur, and variations in the characteristic can be prevented during a long time storage.

Using the surface acoustic wave sensor according to the second preferred embodiment, hydrogen gas was used as an analyte and brought into contact with the surface acoustic wave sensor for 10 minutes, and the change in the resonance frequency was determined. The results thereof are shown in FIG. 8.

Figure 8:
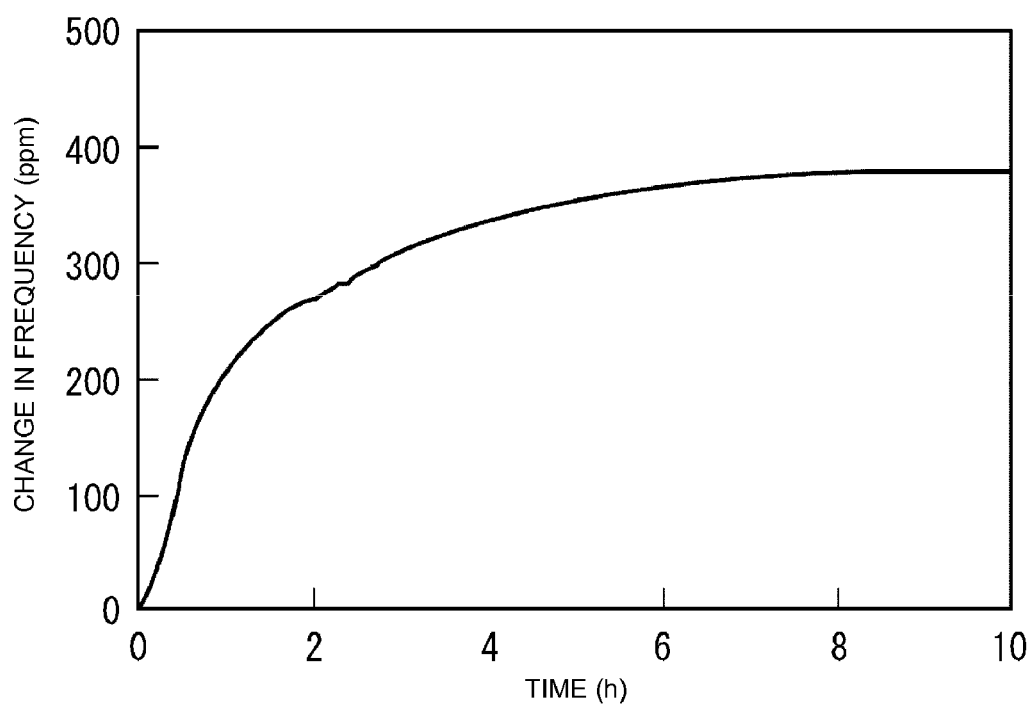
FIG. 8 is a graph showing the change in the frequency characteristic when a gas containing hydrogen gas as an analyte is brought into contact with a surface acoustic wave sensor according to the second preferred embodiment of the present invention.

As is evident from FIG. 8, the resonance frequency changes with time, and in about 8 minutes, the resonance frequency is substantially stabilized. Consequently, according to this preferred embodiment, it is clear that hydrogen gas as a target substance to be detected is occluded by the reaction film, and thereby, the presence or absence and the amount of hydrogen gas can be detected.

Modification Example

Figure 9:
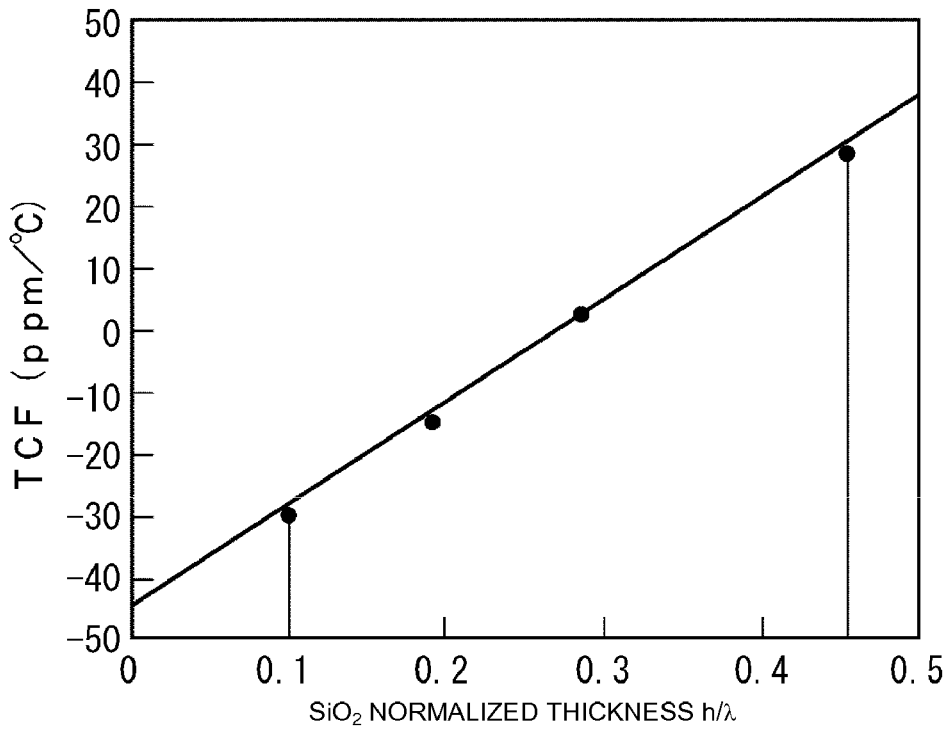
FIG. 9 is a graph showing the change in the temperature coefficient of frequency TCF of a surface acoustic wave sensor when the $SiO_2$ thickness is changed.

In each of the first and second preferred embodiments, the piezoelectric substrate 2 is preferably composed of $LiTaO_3$. The $LiTaO_3$ substrate has a negative temperature coefficient of frequency TCF. The insulating film 6 is composed of $SiO_2$, which has a positive temperature coefficient of frequency TCF. As the thickness of a $SiO_2$ film is changed, the temperature coefficient of frequency TCF of the surface acoustic wave sensor 1 changes. FIG. 9 is a graph which shows, in the case where a surface acoustic wave sensor 1 according to the first preferred embodiment is fabricated using a piezoelectric substrate 2 composed of $LiTaO_3$, the change in the temperature coefficient of frequency TCF of the surface acoustic wave sensor 1 when the thickness of the insulating film composed of $SiO_2$ is changed.

In this case, when the normalized thickness h/λ of the $SiO_2$ film is set in the range of about 0.1 to about 0.45, for example, it is possible to set the absolute value of the temperature coefficient of frequency TCF of the entire surface acoustic wave sensor 1 at approximately 30 ppm/° C. or less, for example. Thereby, good temperature characteristics can be obtained.

Figure 11:
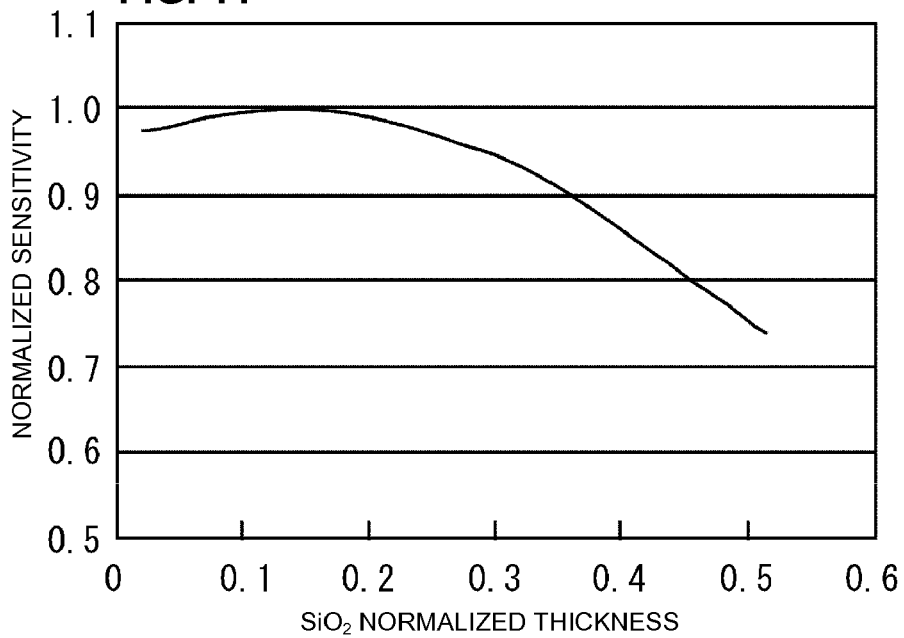
FIG. 11 is a graph showing a relationship between the $SiO_2$ normalized thickness and normalized sensitivity of surface acoustic wave sensors.

FIG. 11 is a graph showing a relationship between the normalized thickness h/λ of the $SiO_2$ film and the normalized sensitivity when the peak of sensitivity is set at 1. As is evident from FIG. 11, at a normalized thickness h/λ of the $SiO_2$ film of about 0.135, the sensitivity reaches the peak, and as the normalized thickness departs from 0.135, the sensitivity decreases. On the other hand, in order to decrease the change in the sensor characteristics due to the change in the temperature of an analyte because of heat generation of the surface acoustic wave sensor, the change in room temperature, or the like, as is evident from FIG. 9, the normalized thickness of the $SiO_2$ film of about 0.27, at which the TCF is 0, is the best.

Furthermore, when a metal film is formed on the $SiO_2$ film, there is a possibility that influences may be caused by the reflection of a bulk acoustic wave at the interface between the $SiO_2$ film and the metal film, the electromagnetic coupling between an electrode located thereunder, such as an IDT electrode or lead electrode, and a bulk acoustic wave, etc. In order to reduce such influences, a normalized thickness of the $SiO_2$ film of about 0.10 or more is preferable, and as the normalized thickness of the $SiO_2$ film increases, the influences decrease.

Therefore, taking into consideration the normalized sensitivity, the change in the characteristic due to the change in temperature, the influences of a bulk surface wave, etc., the normalized thickness of the $SiO_2$ film is preferably in the range of about 0.10 to about 0.45, for example. More preferably, the h/λ is in the range of about 0.10 to about 0.35, for example, because the normalized sensitivity can be set at about 0.9 or more.

Furthermore, in the case of $LiNbO_3$, its temperature coefficient is about 2.5 times the temperature coefficient of $LiTaO_3$, and thus, by setting the normalized thickness of the $SiO_2$ film h/λ in the range of about 0.25 to about 1.125, for example, the absolute value of the temperature coefficient of frequency TCF of the entire surface acoustic wave sensor can be set at approximately 30 ppm/° C. or less, for example. Thereby, good temperature characteristics can be obtained as in the case of $LiTaO_3$.

In the first preferred embodiment, the reaction film is composed of Ni. However, the reaction film 8 may be formed using Cu, Co, or Zn. In such a case, it is also possible to detect a histidine-tagged protein as in the preferred embodiment described above.

Furthermore, in the second preferred embodiment, the reaction film is preferably composed of Pd. However, the reaction film may be formed using a PdNi alloy, a TiFe alloy, or the like instead of Pd. In such a case, hydrogen is also occluded, and thus, hydrogen gas can be detected.

The material constituting the reaction film is not limited to the materials shown in the first and second preferred embodiments, and various metals or metal oxides can be used depending on the target substance to be detected. For example, in order to detect carbon monoxide gas, the reaction film may be formed using a metal or a metal oxide, such as ZnO, SnO, or Pt. In order to detect a nitrogen oxide, a reaction film composed of $ZrO_2$ may be used.

In short, in preferred embodiments of the present invention, in the case where the reaction film is composed of a metal or a metal oxide and the reaction film is formed directly on the insulating film composed of $SiO_2$ or the like, moisture absorption can be prevented and minimized in comparison with the case where a metal film or an insulating film with a h/λ of about 0.1 or more, such as a $SiO_2$ film, is not used. Consequently, as the metal or the metal oxide, various metals or metal oxides capable of reacting with a target substance to be detected by various means, such as adsorption, chemical bonding, or occlusion, or capable of reacting with a binding substance that binds to a target substance to be detected.

Furthermore, with respect to the surface wave exciting electrode structure constituting a resonator-type surface acoustic wave filter, the structure is not limited to the one in which two IDTs and a pair of reflectors are used. Any of various electrode structures of resonator-type surface acoustic wave sensors can be appropriately used.

Furthermore, the insulating film 6 is not limited to $SiO_2$, and may be composed of another insulating material having a positive temperature coefficient of frequency TCF, such as SiN. By using an insulating material having a positive temperature coefficient of frequency TCF, when the insulating film is combined with a piezoelectric substrate having a negative temperature coefficient of frequency, the temperature characteristic of frequency can be improved.

The insulating film 6 is not limited to the insulating material having a positive temperature coefficient of frequency TCF, and may be composed of another insulating material, for example, a resin, such as polyimide or PMMA.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A surface acoustic wave sensor for detecting a mass load on a resonator-type surface acoustic wave filter on the basis of a change in frequency, the surface acoustic wave sensor comprising:
    a piezoelectric substrate;
    a surface wave exciting electrode disposed on the piezoelectric substrate;
    an insulating film arranged on the piezoelectric substrate so as to cover the surface wave exciting electrode; and
    a reaction film arranged on the insulating film to react with a target substance to be detected or a binding substance that binds to a target substance to be detected; wherein the reaction film is composed of a metal or a metal oxide.

2. The surface acoustic wave sensor according to claim 1, wherein the piezoelectric substrate is composed of $LiTaO_3$, the insulating film is composed of $SiO_2$ or SiN, and the thickness of the insulating film normalized by the wavelength of a surface acoustic wave of the surface wave exciting electrode is in a range of about 0.1 to about 0.45.

3. The surface acoustic wave sensor according to claim 1, wherein the piezoelectric substrate is composed of $LiNbO_3$, the insulating film is composed of $SiO_2$ or SiN, and the thickness of the insulating film normalized by the wavelength of a surface acoustic wave of the surface wave exciting electrode is in a range of about 0.25 to about 1.125.

4. The surface acoustic wave sensor according to claim 1, wherein the reaction film is composed of one metal selected from the group consisting of Ni, Cu, Co, and Zn.

5. The surface acoustic wave sensor according to claim 1, wherein the reaction film is composed of one metal selected from the group consisting of Pd, PdNi, and TiFe.

6. The surface acoustic wave sensor according to claim 1, wherein the reaction film is composed of one metal or metal oxide selected from the group consisting of ZnO, SnO, and Pt.

7. The surface acoustic wave sensor according to claim 1, wherein the reaction film is composed of $ZrO_2$.

8. The surface acoustic wave sensor according to claim 1, wherein the surface wave exciting electrode includes, as a main component, a metal that is heavier than Al.

* * * * *